(12) United States Patent
Schlaudraff et al.

(10) Patent No.: US 9,759,551 B2
(45) Date of Patent: Sep. 12, 2017

(54) METHOD FOR CALIBRATING A LASER DEFLECTION APPARATUS OF A LASER MICRODISSECTION SYSTEM AND LASER MICRODISSECTION SYSTEM

(71) Applicant: LEICA MICROSYSTEMS CMS GMBH, Wetzlar (DE)

(72) Inventors: Falk Schlaudraff, Butzbach/Nieder-Weisel (DE); Qing Tang, The Woodlands, TX (US)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 14/913,385

(22) PCT Filed: Aug. 22, 2014

(86) PCT No.: PCT/EP2014/067896
§ 371 (c)(1),
(2) Date: Feb. 22, 2016

(87) PCT Pub. No.: WO2015/028401
PCT Pub. Date: Mar. 5, 2015

(65) Prior Publication Data
US 2016/0202040 A1    Jul. 14, 2016

(30) Foreign Application Priority Data
Aug. 26, 2013   (DE) .................. 10 2013 216 938

(51) Int. Cl.
*G01B 11/14*   (2006.01)
*G02B 21/32*   (2006.01)
(Continued)

(52) U.S. Cl.
CPC ......... *G01B 11/14* (2013.01); *G01N 33/4833* (2013.01); *G02B 21/32* (2013.01);
(Continued)

(58) Field of Classification Search
CPC .. G01B 11/14; G01N 33/4833; G01N 1/2813; G01N 2001/284; G02B 21/32
(Continued)

(56) References Cited

U.S. PATENT DOCUMENTS

| | | | |
|---|---|---|---|
| 7,044,008 B1 | 5/2006 | Schuetze et al. | |
| 2002/0025511 A1* | 2/2002 | Bova | G01N 1/2813 435/4 |

(Continued)

FOREIGN PATENT DOCUMENTS

| | | |
|---|---|---|
| DE | 10018255 C2 | 10/2001 |
| DE | 102007016301 A1 | 10/2008 |

(Continued)

OTHER PUBLICATIONS

Isenberg G., et al.: "Cell surgery by laser micro-dissection: a preparative method", Journal of Microscopy, vol. 107, pp. 19-24, May 1976.

(Continued)

*Primary Examiner* — Sunghee Y Gray
(74) *Attorney, Agent, or Firm* — Leydig, Voti & Mayer, Ltd.

(57) ABSTRACT

A method for calibrating a laser deflection device in a reflected light device of a microscope of a laser microdissection system having a digital image capturing unit comprising an image evaluation module includes generating a laser beam; guiding the laser beam through a microscope objective; directing the laser beam to a position defined by actuation signals; placing a calibration object in the object plane of the microscope objective; actuating the laser deflection device using first actuation signals and first calibration values, making at least one calibration mark on the calibration object; capturing an image of the calibration object by the digital image capturing unit; determining actual position (Continued)

values for the at least one calibration mark: and determining second calibration values based on a relationship between the default position values and the actual position values.

9 Claims, 4 Drawing Sheets (51) Int. Cl.
*G01N 33/483* (2006.01)
*G06T 7/00* (2017.01)
*G01N 1/28* (2006.01)

(52) U.S. Cl.
CPC ...... *G06T 7/0012* (2013.01); *G01N 2001/282* (2013.01); *G01N 2001/2886* (2013.01); *G06T 2207/10056* (2013.01); *G06T 2207/30204* (2013.01)

(58) Field of Classification Search
USPC .......................................................... 356/614
See application file for complete search history.

(56) References Cited

U.S. PATENT DOCUMENTS

| | | |
|---|---|---|
| 2002/0056345 A1 | 5/2002 | Ganser et al. |
| 2002/0164678 A1 | 11/2002 | Ganser et al. |
| 2003/0133190 A1 | 7/2003 | Weiss |
| 2006/0186349 A1 | 8/2006 | Weiss |
| 2007/0066967 A1 | 3/2007 | Sieckmann et al. |
| 2008/0194011 A1 | 8/2008 | Wesner |
| 2014/0190946 A1 | 7/2014 | Gögler |

FOREIGN PATENT DOCUMENTS

| | | |
|---|---|---|
| DE | 102007046267 A1 | 4/2009 |
| EP | 1186879 A2 | 3/2002 |
| EP | 1276586 B1 | 1/2003 |
| EP | 1719998 B1 | 11/2006 |
| WO | WO 9711156 A2 | 3/1997 |
| WO | WO 9814816 A1 | 4/1998 |
| WO | WO 9928725 A1 | 6/1999 |
| WO | WO 0173398 A1 | 10/2001 |
| WO | WO 0178937 A1 | 10/2001 |
| WO | WO 2006134142 A1 | 12/2006 |
| WO | WO 2012126961 A1 | 9/2012 |

OTHER PUBLICATIONS

Bancroft, J.D. and Gamble, M.: "Theory and Practice of Histological Techniques", Elsevier Science, p. 575, chapter "Laser Microdissection", Oct. 26, 2012.

* cited by examiner

METHOD FOR CALIBRATING A LASER DEFLECTION APPARATUS OF A LASER MICRODISSECTION SYSTEM AND LASER MICRODISSECTION SYSTEM

CROSS REFERENCE TO RELATED APPLICATIONS

This application is a U.S. National Stage Application under 35 U.S.C. §371 of International Application No. PCT/EP2014/067896 filed on Aug. 22, 2014, and claims benefit to German Patent Application Nos. DE 10 2013 216 938.8 filed on Aug. 26, 2013. The International Application was published in German on Mar. 5, 2015 as WO 2015/028401 A1 under PCT Article 21(2).

FIELD

The present invention relates to a method for calibrating a laser deflection device of a laser microdissection system and to a laser microdissection system.

BACKGROUND

Methods for processing biological samples by means of laser microdissection have existed since the mid-1970s (see e.g. Isenberg, G. et al.: Cell surgery by laser microdissection: a preparative method, Journal of Microscopy, volume 107, 1976, pages 19-24) and have since been continuously developed.

In laser microdissection, cells, tissue regions, etc. can be isolated from an object (e.g. a "sample," or a "preparation") and extracted as dissection specimens. A particular advantage of laser microdissection is the brief contact between the object and the laser beam, as a result of which said object is barely modified. The specific extraction of the dissection specimens can be carried out in various ways (see e.g. Bancroft, J. D. and Gamble, M.: Theory and Practice of Histological Techniques, Elsevier Science, 2008, page 575, "Laser Microdissection" chapter).

For example, in known methods, a dissection specimen can be isolated from an object by means of an infrared laser beam or ultraviolet laser beam, which specimen falls into a suitable dissection specimen collection container under the influence of gravity. The dissection specimen can also be cut out of the object in this case, together with an adherent membrane. In laser capture microdissection, however, a thermoplastic membrane is heated using a corresponding laser beam. In this case, the membrane fuses with the desired region of the object and can be removed by means of tearing in a subsequent step. A further alternative is that of attaching the dissection specimen to a lid of a dissection specimen collection container by means of the laser beam. In known inverse microscope systems for laser microdissection, dissection specimens which are ejected upwards can also be attached to the base of a dissection specimen collection container which is provided with an adhesive coating.

Known microscope systems for laser microdissection, as are known from WO 98/14816 A1 for example, comprise a reflected light device, into the beam path of which a laser beam is coupled. The laser beam is focussed on the object through the microscope objective used in each case, which object is rests on a microscope stage which can be automatically moved by means of a motor. A cutting line is produced by the microscope stage being moved during cutting, in order to move the object relative to the stationary laser beam. However this has the disadvantage, inter alia, that it is not easy to observe the object while the cutting line is being produced, since said object moves in the field of vision and the image thereof may appear blurred.

Laser microdissection systems which have laser deflection devices and laser scanning devices designed to direct the laser beam or the point of impingement of said beam over a stationary object are therefore more advantageous. Laser microdissection systems of this kind, which also provide particular advantages within the scope of the present invention, are explained in detail hereinafter. A particularly advantageous laser microdissection system having a laser deflection device, which comprises glass wedges in the laser beam path which can be adjusted relative to one another, is described in EP 1 276 586 B1 for example.

In both cases, i.e. in both laser microdissection systems in which the microscope stage is moved and laser microdissection systems comprising a laser deflection device, pulsed lasers are generally used, each laser pulse creating a hole or depression in the object. A cutting line is produced as a result of a series of successive, and possibly overlapping, holes or depressions of this kind. Laser microdissection can be used to extract individual cells or defined tissue regions which then undergo different diagnostic analysis methods, for example. In oncology, laser microdissection can be used, for example, to isolate specific tumour cells from a microscopic cut and examine them for specific metabolites or proteins. In this case, it has to be ensured that no material or as little material as possible from undesired and possibly interfering regions of the examined object reaches an examination vessel and therefore interferes with a corresponding analysis. This also applies to laser microdissection systems which are used for molecular biological examinations, for example for known COMET assays.

The accuracy of the laser used is therefore crucial for successful and uncontaminated laser microdissection experiments. The more accurately the laser is able to cut, for example with the aid of predefined cutting lines, or can be guided over the region in question with precise accuracy, the cleaner the extraction of corresponding material.

The laser of a laser microdissection system or a corresponding laser deflection device therefore has to be calibrated as accurately as possible, so that default position values, which indicate target positions for the points at which the laser impinges on the sample, and the resulting actual position values, i.e. the actual points of impingement, differ from one another as little as possible.

Common calibration methods are, however, often not sufficiently reliable or exact and/or are very complex for a user to carry out.

SUMMARY

In an embodiment the present invention provides a method for calibrating a laser deflection device in a reflected light device of a microscope of a laser microdissection system including a digital image capturing unit comprising an image evaluation module. The method includes: generating, by a laser unit of the laser microdissection system, a laser beam; guiding the laser beam through a microscope objective of the microscope by the reflected light device; directing the laser beam to a position, which is defined by actuation signals, in an object plane of the microscope objective on the laser deflection device; placing a calibration object in the object plane of the microscope objective; actuating the laser deflection device using first actuation signals which are calculated on the basis of default position values and first calibration values; making at least one calibration mark on the calibration object using the laser beam; capturing an image of the calibration object by the digital image capturing unit; determining actual position values for the at least one calibration mark by the image evaluation module; and determining second calibration values based on a relationship between the default position values and the actual position values.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

In view of the above, an embodiment of the present invention provides a method for calibrating a laser deflection device of a laser microdissection system and a laser microdissection system.

An embodiment of the present invention can be used in methods in which a dissection specimen is separated from an object and collected in a dissection specimen collection container arranged below said object. In particular, an embodiment of the invention is suitable for contactless systems for collecting dissection specimens.

An embodiment of the invention proceeds from a method for calibrating a laser deflection device arranged in a reflected light device of a microscope of a laser microdissection system. By means of the laser deflection device, a laser beam, which is generated by a laser unit of the laser microdissection system and is guided through a microscope objective of the microscope by the reflected light device, is directed to a position, in an object plane of the microscope objective, on the laser deflection device which is defined by actuation signals. A corresponding laser microdissection system further comprises a digital image capturing unit comprising an image evaluation module.

According to an embodiment of the invention, a calibration object is placed in the object plane of the microscope objective. The laser deflection device is then actuated using first actuation signals which are calculated on the basis of default position values and using first calibration values. By activating the laser beam, at least one calibration mark is made on the calibration object either during or, in each case, after the actuation by means of the actuation signals which can in particular also be combined to form signal sequences. The calibration object is then captured by the digital image capturing unit and actual position values for the at least one calibration mark are determined by the image evaluation module. Second calibration values are determined on the basis of a relationship between the default position values and the actual position values.

A user can specify default position values, for example by means of a computer mouse or another suitable input device on a computer screen. These are generally target position values which indicate positions at which the laser beam or a focal point of the laser beam produced through a microscope objective are intended to impinge upon an object. In conventional laser microdissection systems, the actuation signals for the laser deflection device can also be calculated from these default position values. Corresponding actuation signals are applied to the laser deflection device.

In this case, actuation signals can be any signals which allow for deflection of a laser beam by means of the above-mentioned laser deflection unit in any desired direction relative to an axis of the microscope objective, and therefore also in the object plane, or based on said plane. The range of movement and movement speed can be determined by the technical limitations of a corresponding laser microdissection. Actuation signals may, for example, comprise numerical actuation values for a control unit assigned to the laser deflection unit, and/or analogue or digital signals for the actuators of a corresponding laser deflection unit, e.g. step motors or piezoelectric motors of a wedge plate arrangement.

Actual position values indicate the actual points of impingement of the laser which result from a corresponding actuation and which unavoidably deviates from the default position values, at least to a certain extent. In this case, the aim of a corresponding calibration is to provide calibration values which reduce the deviations between the default position values and the resulting actual position values as much as possible. The calibration values are included in the calculation of the actuation signals in this case.

A relationship between the default position values and the actual position values, for example a deviation between the elements of tuples used to describe the position, is used for the calibration. The actual calibration comprises determining values (calibration values) for a transformation specification from such a relationship, by way of which specification the default position values and the actual position values can be brought into alignment. The calibration values may then be used at any point in a calculation method for calculating the actuation signals. For example, these values (in accordance with known pilot control methods) may be offset against the default position values such that the actuation signals are calculated using correspondingly adapted default position values. Within the context of the method proposed herein, a calibration method thus compensates for a deviation between target and actual values by way of a suitable calculation specification. In the simplest case, this can merely be an addition or subtraction of coordinate values, as a result of which the corresponding coordinates are displaced homogeneously. In cases in which a plurality of calibration marks are made on a calibration object and in which various deviations result between the calibration marks or the actual position values determined using said marks and the default position values it may, however, be necessary to use an adapted, optionally interpolating, calculation specification over the entire viewed region, which allows for as precise a transformation as possible of all values.

An embodiment of the invention thus proceeds from a laser microdissection system that includes a microscope having a reflected light device, a microscope objective and a laser unit, a beam path of a laser beam from the laser unit extending through the reflected light device and through the microscope objective and intersecting an object plane of the microscope objective at an adjustable intersection point which is specified to the laser deflection device by means of actuation signals.

An embodiment of the invention can be used in particular in contactless laser microdissection systems which may be characterised by a dissection specimen falling downwards out of the object as a result of gravity, rather than being attached to membranes and the like. In this case, the object is arranged in upright systems on the underside of a microscope slide and is processed through the microscope slide, from the upper side thereof.

By way of the reflected light device, a laser beam from a laser light source is therefore coupled into the observation beam path of the microscope. The laser beam is focussed on the object through the microscope objective which is also used to view the object.

In order to prevent any misunderstandings, it should be emphasised here that the laser microdissection system used within the context of the invention can be used with objects which have already been prepared so as to be suitable for microscopy. This can be, for example, thin cuts which are separated from a larger tissue block by a microtome. A tissue block of this kind can be a fixed organ or a biopsy of a corresponding organ, for example. The laser microdissection system according to the invention is therefore not used to extract objects but to process them and to isolate specific regions thereof. It is clear that the invention can also be used with objects which are not extracted by a microtome, e.g. with smears, macerations, etc.

Microtomes are only used for preparing microscopic objects. Microtomes can also comprise lasers for this purpose. The cuts made by means of a microtome are placed on a microscope slide, as mentioned above, optionally fastened thereto and stained, etc. Only then are they available for use in the laser microdissection system. A microtome fundamentally differs from a laser microdissection system in terms of its operation, inter alia, in that cuts are extracted here using as homogenous a cutting thickness as possible. Microtomes are therefore designed to produce a large number of identical cuts having parallel cutting surfaces, whereas laser microdissection systems are designed to remove dissection specimens in accordance with object-dependent criteria, for example in accordance with visual criteria. A person skilled in the art would therefore not apply technical solutions used for microtomes to laser microdissection systems.

Microtomes do not comprise a microscope either, into the observation beam path of which a laser beam is coupled. In microtomes, the laser beam is therefore also never focussed on an object, e.g. a tissue block, through a microscope objective which is also used for viewing purposes.

In laser microdissection systems having a laser deflection device, as used in accordance with the invention, when removing the dissection specimen, i.e. during the dissection process, the microscope stage is fixed in position in relation to the microscope objective with regard to the x-y direction (i.e. in the directions perpendicular to the optical axis of the microscope objective).

In comparison to laser microdissection system having a microscope stage (scanning stage) which is moved by a motor during the dissection process and which has to have high positioning accuracy in particular for highly magnifying objectives in order to allow for precise cuts, the laser microdissection systems having a laser deflection device have proven to be simpler and less expensive to manufacture and have advantages in terms of precision.

In an embodiment, the laser deflection device comprises two thick glass wedge plates ("glass wedge") which are inclined with respect to an optical axis, can be rotated independently of one another about an optical axis and produce a beam deflection as a result of the wedge angle thereof. By rotating the glass wedge plates, the resulting deflection angle of the laser beam relative to the optical axis is variable. At the output of the laser deflection device, the laser beam has a lateral beam offset in relation to the optical axis as a result of the thickness and inclination of the glass wedge plates and, for all deflection angles, impinges on the centre of the objective pupil of the microscope objective. The intersection point between the laser beam and the object plane is therefore adjustable.

A laser deflection device of this type is therefore advantageous in particular over other laser deflection devices such as mirror scanners, galvanometer scanners or stepper motor scanners, on account of the fact that this type of laser deflection device does not have to be arranged in a plane which is conjugate with the objective pupil. Pupil imaging is thus not required either in order for the deflected beam to impinge on the object pupil. In microdissection using UV laser light, for example UV-suitable pupil imaging would be necessary. Further advantages of a laser deflection device comprising wedge plates are disclosed, for example, in EP 1 276 586 B1.

A method according to an embodiment of the invention is particularly advantageous if planar coordinates and/or polar coordinates in one reference plane are used for the default position values, the actual position values and/or the calibration values. The object plane, a surface of an object, a surface of an object stage and/or any other real or virtual plane of the laser microdissection system can be used as the reference plane, for example. Corresponding planar coordinates and/or polar coordinates relate in each case to a reference point which is fixed in the reference plane or is in a fixed spatial relationship therewith. Planar coordinates are understood to mean standard x-y coordinates in this case ("easting and northing" or corresponding data) which relate to the particular reference point. However, polar coordinates define a position in space (or in the reference plane in this case) over an angle and a distance from the particular reference point. The planar coordinates and polar coordinates do not necessarily have to be presented to the user in their raw state. Corresponding planar coordinates and/or polar coordinates can instead also be internally calculated in the system from user specifications, for example from lines which the user defines using a computer mouse around the region in question of a digitally depicted object.

An embodiment of the present invention allows for automatic calibration of the laser beam without user intervention as a result of the automatic recognition by means of the image evaluation module of the digital image capturing unit, and of the laser beam control by means of the laser deflection unit. Incorrect operation by the user is therefore not possible; calibration of the laser beam is significantly more accurate than in conventional methods or laser microdissection systems, as form the basis of EP 1 186 879 A1 for example, due to the objective and reproducible pattern recognition.

In conventional methods or laser microdissection systems, the laser or the laser deflection device thereof can be calibrated by hand on the basis of reference crosses. Manual calibration method comprises making calibration marks on a calibration object. However, these marks then have to be marked by hand on the basis of a digital image using a computer mouse. This method is not completely reliable and is dependent on the particular user, their experience and accurately determining the calibration marks. In certain circumstances this may result in greatly deviating calibrations, which are disadvantageous in particular with regard to the reproducibility and certifiability of a corresponding method, for example in medical diagnostics. In addition, repeating the calibration as a result of incorrect calibrations costs time unnecessarily.

An embodiment of the present invention is particularly advantageous if at least two, but in particular three or more calibration points in the form of calibration marks are used to calibrate the laser beam or the laser deflection device. In known calibration methods, four calibration crosses are typically used to manually calibrate the software-assisted laser beam control using a corresponding laser deflection device. For this purpose, one cross is first cut by the laser, in a suitable object which is in the focus of the laser and therefore of the microscope objective, in a certain position, conventionally at the top right-hand side of the field of vision. The centre of this cross is then marked by hand by means of the mouse or a touchscreen. Another cross is then cut in the object using the laser in another position (top left). The second cross is in turn marked by hand in the same way as the first cross. The aforementioned steps are then repeated using crosses cut by the laser in additional positions (bottom right and bottom left), together with a corresponding manual mark in each case. A method of this kind is simplified and made more accurate by the present invention.

An embodiment of the invention makes it possible to recognise in a fully automatic manner the calibration marks made in the calibration object and to calculate a pixel-accurate centre point. This can automatically be stored and forwarded for the calibration. The aforementioned method is very accurate on account of the automatic calculation and forwarding of the centre point to a piece of laser microdissection control software of the laser focus unit and/or the laser deflection unit.

The method can be simplified by isolating the region for the particular recognition of the calibration marks (e.g. of laser crosses or laser points) beforehand. In this case, as also shown in FIG. 4 for example, only the centre of the field of vision can be used for a fixed laser and/or first the upper right-hand region, then the upper left-hand region, then the lower right-hand region and the lower left-hand region of the field of vision can be used for the recognition if a calibration mark has been made beforehand in each region. This reduces errors.

As mentioned, calibration is particularly accurate when at least three calibration marks are made on the calibration object and actual position values are determined therefrom. The accuracy of the calibration proposed by an embodiment of the invention can be further increased if a special calibration object is used which has a coating which can be processed by the laser beam and is applied to a microscope slide. For example, a coating of this kind can, in comparison with an object to be subsequently processed, be selected such that as fine a line as possible can be produced by means of the laser beam, which line simultaneously provides a sufficient contrast during irradiation by the laser beam. A coating of this kind can also be provided with suitable photoreactive and/or thermoreactive pigments which change colour due to irradiation by the laser. This makes it possible to make coloured calibration marks which can be easily captured, e.g. by colour-selective recognition specifications, in a corresponding image capturing unit or an image recognition module of an image capturing unit of this kind.

Calibration objects which can be used here are monochrome calibration slides, for example. An otherwise empty microscope slide having a laser-processable membrane can be used here, for example. The membrane is advantageously provided with a coloured coating which can be removed or decoloured by laser processing in order to add contrast. In the simplest case, a corresponding membrane can for example be provided with a suitable colour coat by a user. Other samples provided with a regular or monochrome surface are also advantageous for fast and automatic calibration since they provide image information, which is very simple to process, for the advantageously performed automatic pattern evaluation.

Photoreactive and/or thermoreactive pigments can be fluorescent dyes, for example, which can be excited using laser radiation in the UV or IR range. In this way, for example, laser calibration is possible in different types of illumination (bright field, phase contrast, fluorescence; cf. EP 1 719 998 B1). Furthermore, special objects having a different coloured surface and which are coated in black or another colour (e.g. a colour coat applied by a user) can be used. In this case, the colour selection can be adapted to the output position of the microscope stage or the microscope slide on the stage, for example. In this case, different exposed colours for example can be used to identify the sequence of the calibration marks or the shapes thereof, which in turn saves time.

In general, a calibration object is any object on which corresponding calibration marks can be made. These objects may be subsequently processed objects, the calibration marks being made in particular in regions which are not required for subsequent analysis, or may be special "calibration slides".

In a method according to an embodiment of the invention, punctiform, circular and/or crosshair-shaped or cross-shaped calibration marks can advantageously be made on the calibration object. It is possible and advantageous to make punctiform calibration marks, in particular when using fixed lasers. The shapes of calibration marks, for example circular, cross-shaped and/or crosshair-shaped calibration marks can be "taught" into a corresponding image evaluation module, allowing for particularly reliable and fast recognition.

A method according to an embodiment of the invention comprises using the second calibration values to calculate actuation signals on the basis of default position values when the laser microdissection system is in post-calibration mode. "Post-calibration mode" is the standard mode of operation of such a laser microdissection system, for example for routine examination or processing of biological or medical objects. Such a post-calibration mode of operation can be implemented up until, for example as a result of deteriorating quality criteria, new calibration is required. In this case, the "second" calibration values can be replaced with newly determined ("third," etc.) calibration values.

As explained above, the image evaluation module can use at least one digital pattern recognition specification when determining the actual position values of the at least one calibration mark. Corresponding pattern recognition specifications are known in principle and disclosed in US 2007/0066967 A1, for example.

The above-mentioned image recognition specifications, with regard to which detailed reference is made to the above-mentioned document US 2007/0066967 A1, can, for example, also comprise shading correction, grey image processing, conversion into a binary image, binary image processing, segmentation and determining object features, for example of the calibration marks and other methods known from the field of image processing.

In particular, an electronic image at least of one image portion of an object is taken and then examined by means of image analysis. In the cited document, US 2007/0066967 A1, at least one dissection specimen to be cut out is automatically determined and a target cutting line is automatically determined around said dissection specimen. Within the scope of the present invention, this technique is applied to a calibration mark and used to determine the actual position values.

Image-analytical methods are usually based on a feature analysis. In this approach, use is made of the fact that each image element, a calibration mark in the present case, can be captured and classified by means of a certain number of individual features. Features may be, for example, variables such as surface area, size and diameter, as well as mass, texture, colour, shape, etc. An image element can be classified and distinguished from other image elements by selecting a suitable set of features.

This suitable set of features is usually plotted in an n-dimensional feature space, as described in detail in the aforementioned document. For example, a feature space having the features colour, surface area and diameter can be selected. Within the scope of the present invention, the feature spaces used can be adapted specifically to the calibration marks, and vice versa. Image elements having comparatively less colour and a small diameter and a small surface area are then classified, for example, by a first feature cluster. Image elements which are captured by another feature cluster are distinguished from said first image elements. For example, the latter image elements can have a comparatively large amount of colour and a small diameter and a small surface area. Additional image elements can be described by yet another feature cluster and have, for example, less colour and a large diameter and a large surface area, etc. Making the calibration marks, as described above, in particular using the above-mentioned shapes or possibly colours and coating of the calibration object, simplifies distinguishing the calibration marks from other image elements which are likewise present on corresponding calibration objects.

In order to recognise the calibration marks, a superimposed image and/or subtraction image consisting of individual images can furthermore also be used both prior to and after the calibration marks have been made, as a result of which the calibration marks can then also be quickly located if their shape is unknown. Furthermore, a corresponding superimposed image and/or subtraction image can be used to calculate an exact centre point of a laser focus.

In accordance with an embodiment of the present invention, the laser can also be automatically adjusted during calibration using the calibration mark and/or the shape thereof. This adjustment includes all adjustable laser parameters, but at least laser energy, cutting speed, aperture and/or frequency. The individual parameters can be adapted depending on the evaluation of the shape and structure of the calibration marks. For example, less energy and a small aperture can be used in the case of lines of the calibration marks being too wide, and a slow speed can be used in the case of "curved" lines which may occur due to an excessive laser guidance speed. Adjusting the aperture of a corresponding laser is known from DE 100 18 255 C1, for example.

The aforementioned features and advantages relate in the same way to a laser microdissection system as proposed by the invention. Said system comprises a microscope having a reflected light device for guiding a laser beam, which is generated by a laser unit of the laser microdissection system, through a microscope objective of the microscope, and a laser deflection device for deflecting the laser beam to an extent defined by actuation signals. The laser microdissection system further comprises a digital image capturing unit comprising an image evaluation module.

According to an embodiment of the invention, the laser microdissection system is provided with a calibration arrangement for calibrating the laser deflection device. This is suitable for actuating the laser deflection device using first actuations signals, which are calculated on the basis of default position values and using first calibration values, by making at least one calibration mark on a calibration object, which is placed in an object plane of the microscope objective, using the laser beam, by subsequently capturing the at least one calibration mark using the digital image capturing unit, by determining actual position values for the at least one calibration mark using the image evaluation module and by determining second calibration values on the basis of a relationship between the default position values and the actual position values determined.

In particular, a laser microdissection system of this kind is designed to carry out a method as described above.

By means of the laser microdissection system according to an embodiment of the invention, desired individual cells or tissue regions (cell networks) of an object can be transferred to a collection vessel and examined in a targeted manner much more precisely in comparison to the prior art. The individual cells or tissue regions can be assigned to clearly defined regions of the object, contaminants being reduced on account of the significantly increased cutting accuracy of the laser. The object can be, for example, a cut from a solid tissue, a smear or swab, for example a microscopic cut through an organ, adherent cell cultures or the like.

Figure 1:
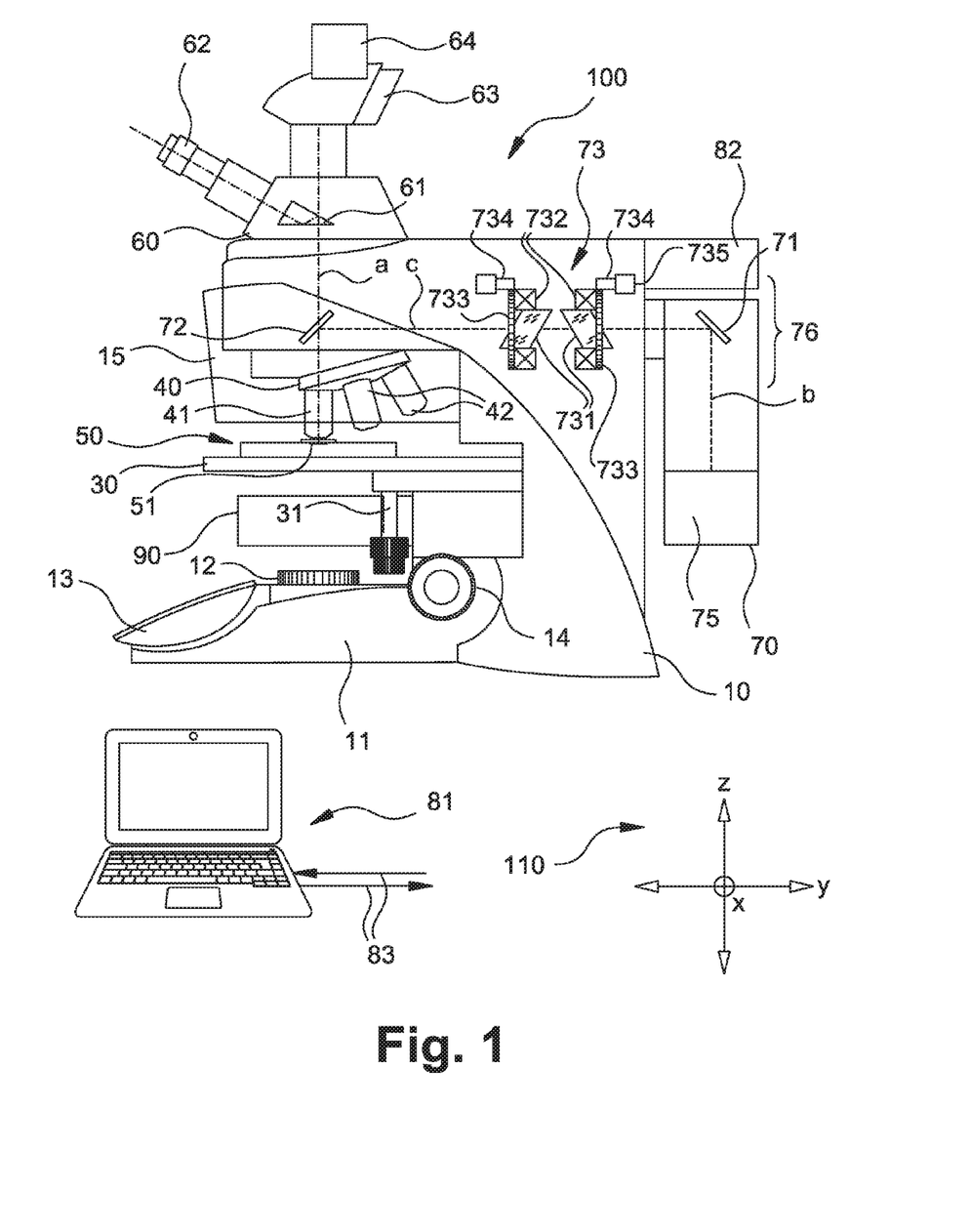
FIG. 1 is a schematic view of a laser microdissection system which can be used to carry out a method according to an embodiment of the invention.

FIG. 1 is a schematic view of a laser microdissection system which can be used to carry out a method according to an embodiment of the invention and which is denoted as a whole by reference numeral 100. The laser microdissection system 100 substantially corresponds to that disclosed in EP 1 276 586 B1, to which reference is explicitly made here. A coordinate system, by means of which the axes or directions x, y and z mentioned below are depicted, is denoted in FIG. 1 by reference numeral 110.

The laser microdissection system 100 comprises a microscope 10. An illumination device 12 (only shown in part in this case) can be provided in a microscope foot 11 of the microscope 10. This device can, for example, comprise a light source and suitable means for influencing the illumination light provided by the light source, for example filters and/or diaphragms. For transillumination and in order to adjust suitable contrast methods or observation methods, a condenser unit 90 may be provided.

A user input unit and/or user information unit 13 can also be arranged on the microscope foot 11, for example, which unit can be formed for example as a touchscreen and by means of which the user can input and/or read out viewing and/or processing parameters, for example.

Furthermore, a pinion knob 14 is provided. This is used for controlling a coarse and fine adjustment for setting the height of a microscope stage 30. An object which is on an microscope slide (not provided with a reference numeral here) on an object holder 50, for example a cut applied to the microscope slide, can be placed in an object plane 51 of an objective 41 as a result thereof. The objective 41 is attached in a rotating nosepiece 40 in addition to further objectives 42. A protective cover 15 may be provided for protection against laser radiation.

Observation light proceeding from the object in the object plane 51 extends along an observation beam path a. In a tubular unit 60 having suitable decoupling devices 61, a preferably variable portion of the observation light, for example approximately 60°, can be decoupled and presented to a user by means of a pair of eyepieces 62. An additional portion of the observation light can be coupled into a digital image capturing unit 63 and captured so as to form an image. In a control unit 82 or a control terminal 81 (see below) or in another spatial arrangement, an image evaluation module 64 can be assigned, on site, to the image capturing unit 63.

The laser microdissection system 100 comprises a laser unit 70 having a laser light source 75. A laser beam b provided by the laser light source 75, which can be a UV laser light source for example, is deflected in a reflected light unit, indicated here as a whole by reference numeral 76, on a first deflection mirror 71 and a second deflection mirror 72 and focussed through the objective 41 onto the object in the object plane 51.

In the laser microdissection system 100, the location at which the laser beam b impinges on the object in the object plane 51 can in principle be adjusted in different ways. On the one hand, a manual adjustment device 31 may be provided, by means of which the microscope stage 30, designed as an XY stage, can be adjusted in the x and y direction (i.e. in this case, perpendicularly to the paper plane and in parallel with the paper plane respectively). In addition to the adjustment device 31, electromechanical actuation means can also be provided and can be actuated by a control 82, for example, or the position thereof can be captured by the control unit 82.

The control unit 82 can also control any additional motorised functions of the laser microdissection system 100 and in particular provide an interface to an external actuation control terminal 81, which can be connected via corresponding connections 83.

A laser deflection device 73 can in particular be provided for the laser microdissection. By means of the laser deflection device 73, the laser beam b can be deflected relative to an optical axis c extending between the first deflection mirror 71 and the second deflection mirror 72. The laser beam can therefore impinge in different positions on the second deflection mirror 72, which can be in the form of a dichromatic divider for example, and is therefore also focussed in different positions on the object in the object plane 51. Deflection by means of a laser deflection device 73 is shown in detail in EP 1 276 586 B1. It should be emphasised that different possibilities for deflecting a laser beam b or for positioning the object in the object plane 51 relative to the laser beam b can be used in this case. The invention is not limited to the example shown.

In the example shown, the laser deflection device 73 comprises two solid glass wedge plates 731 which are inclined relative to the optical axis c and can be rotated independently of one another about the optical axis c. For this purpose, the wedge plates 731 are mounted using ball bearings 732. Each of the wedge plates is connected to a gear wheel 733.

Each of the gear wheels 733 can be rotated by means of actuators 734 to which corresponding actuation signals can be applied and which drive the gear wheels 733 accordingly. The actuators 734 can have position transmitters 735 (only shown on the right-hand actuator 734 in this case). A position detected by the position transmitters 735 can be transmitted to the control unit 80.

Figure 2:
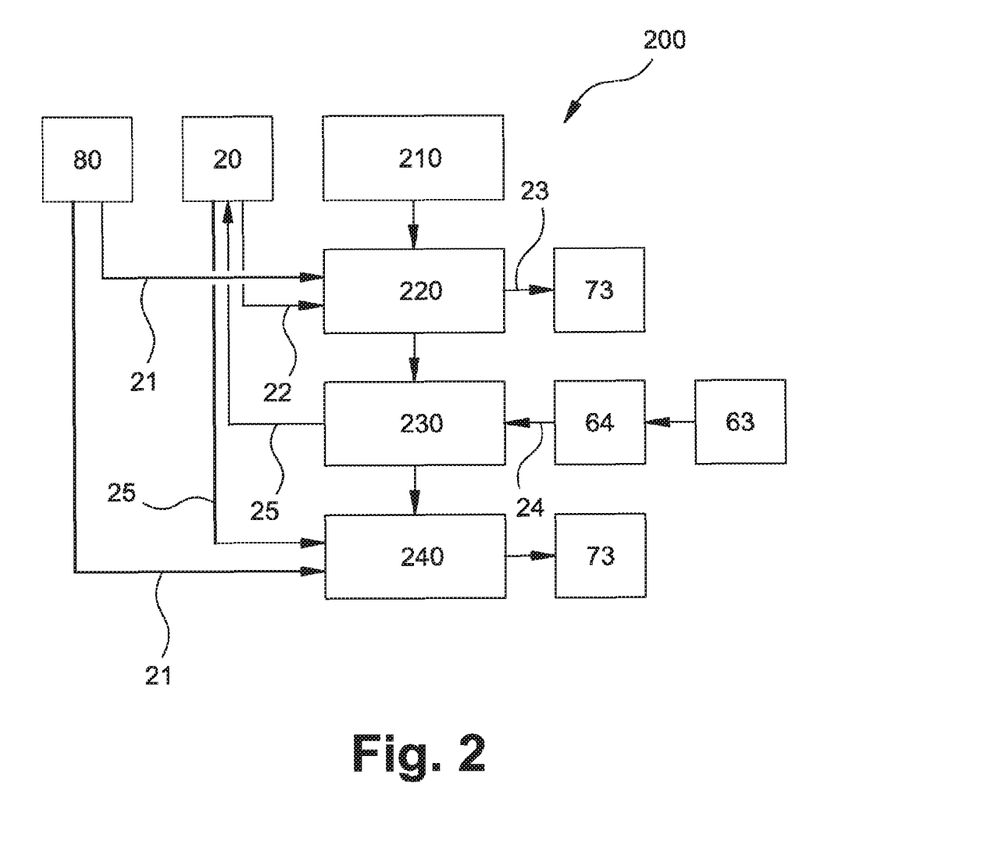
FIG. 2 is a schematic view of a method for calibrating a laser deflection device according to one embodiment of the invention.

FIG. 2 is a schematic flowchart, denoted as a whole by reference numeral 200, of a method according to a particularly preferred embodiment of the invention. The method 200 is implemented in a laser microdissection system configured for this purpose, for example the laser microdissection system 100 shown in FIG. 1.

The method proceeds from a step 210 in which a corresponding laser microdissection system is uncalibrated. As explained above multiple times, in this uncalibrated state it cannot be ensured that the above-mentioned default position values and actual position values correspond to one another to the required extent. In order to ensure this, the calibration method 200 is carried out.

In a step 220, for this purpose the above-mentioned default position values 21 are specified by means of a control unit 80, for example. These are target values which indicate a desired position of the laser beam in the object plane 51 of the microscope objective 41. In the step 220, the specified position values 21 are also offset against "first" calibration values 22, which are called up from a calibration data store 20 for example. The calibration data 22 used in step 220 can be, for example, standard calibration data, as are typically used for a corresponding laser microdissection system, or calibration data which are available after relatively long operation of a corresponding laser microdissection system 100. In step 220, actuation signals 23 are calculated from the default position values 21 and the calibration values 22 and are issued to a laser deflection unit, for example the laser deflection unit 73 of the laser microdissection system shown in FIG. 1. These signals can in particular also be corresponding signal sequences of actuation signals 23 which cause continuous and/or stepwise deflection of the laser in the laser deflection unit 73. At the same time (not shown), a corresponding laser is activated in a continuous or pulsed manner such that at least one calibration mark can be produced by the laser beam on a calibration object, which is placed in an object plane 51 of the microscope objective 41. After successful completion of step 220, by means of which a desired number of corresponding calibration marks have been made on the calibration object, the method is continued in a step 230.

In step 230, the calibration object 52 which is placed in the object plane 51 of the microscope objective 41 is captured digitally by a digital image capturing unit, for example the digital image capturing unit 63 of the laser microdissection system 100 shown in FIG. 1. By means of an image evaluation module 64 assigned to the digital image capturing unit 63, actual position values 24 for the at least one calibration mark 53 are determined in this case. These values are correlated with the default position values 21 in step 230. For example, an x and y deviation in the object plane between the default position values 21 and the actual position values 24 is determined. On the basis thereof, new ("second") calibration values 25 are then determined and transferred to the calibration data store 20. In this case, the original ("first") calibration values 22 for example are overwritten by the newly determined ("second") calibration values 25.

The laser microdissection system 100 is therefore calibrated, as shown in step 240. In this step 240, for the purpose of laser microdissection, corresponding default position values 21 are likewise specified, for example by the control unit 80, but then offset against the newly determined calibration values 25. Actuation signals (not provided with a reference numeral in this case) which are calculated on the basis thereof can be issued to the laser deflection device 73 and improve consistency between the default position values and the actual position values.

Figure 3A:
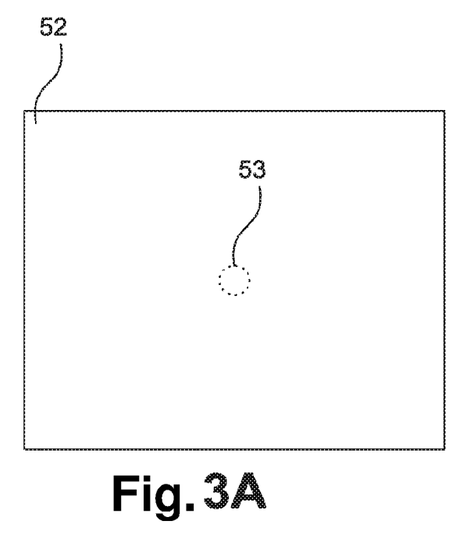
FIGS. 3A and 3B are schematic views of calibration marks for calibrating a laser deflection device according to one embodiment of the invention.
Figure 3B:
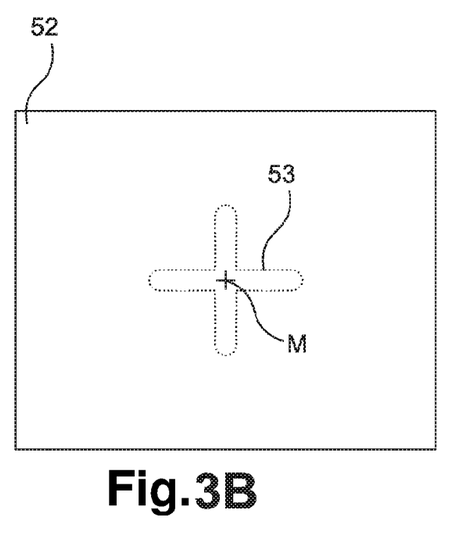

FIG. 3 is a significantly enlarged view of alternative shapes of calibration marks 53 on calibration objects 52. FIG. 3A shows a punctiform calibration mark 53 which is made, for example, in the centre of a calibration object 52 when a fixed laser beam is used, as also explained above. FIG. 3B shows a calibration mark 53 which can be made by means of a laser deflection device 73 and is in the shape of a cross in the example shown. An image evaluation routine, for example suitable parameterised digital evaluation means, implemented for example in a digital image capturing unit 63 or in an image evaluation module 64 of a digital capturing unit 63 of this kind, can be designed to recognise corresponding shapes of calibration marks 53 on calibration objects 52. A characteristic shape such as the cross shape shown in FIG. 3B makes the recognition easier. Furthermore, by means of a corresponding shape, a reference point defined thereby, for example the centre point M in this case, can be defined in a particularly simple manner.

FIG. 4 is a schematic view of the sub-figures 4A to 4D of consecutive sub-steps of a method according to a particularly preferred embodiment of the invention. In all of the sub-figures 4A to 4D, as in the sub-figures 3A and 3B in FIG. 3, calibration objects 52 which are captured by means of a digital image capturing unit 63 are shown in portions.

Figure 4A:
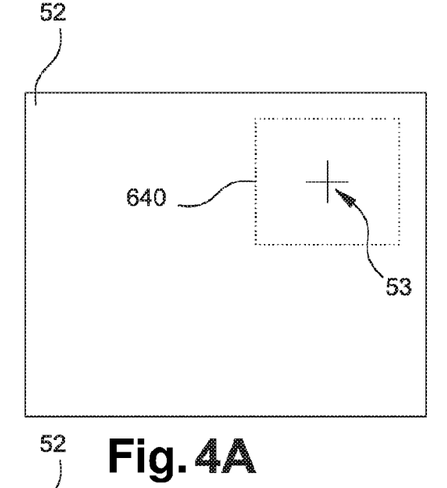
FIGS. 4A, 4B, 4C and 4D are schematic views of a method for calibrating a laser deflection device according to one embodiment of the invention.

In the first sub-step shown in FIG. 4A, a corresponding calibration mark 53 is made in an upper right-hand corner of the calibration object 52. A region evaluated by an image evaluation module 64 is denoted by reference numeral 640 here and is outlined by a dotted line. Inside the region 640, an image evaluation module evaluates the available image data using the calibration mark 53 contained therein and determines an actual position value on the basis thereof. The actual position value can be indicated for example in the form of x and y image coordinates which correspond to defined coordinates of the calibration object 52 in a correspondingly calibrated image evaluation module. If the sub-step shown in FIG. 4A is successfully completed and if actual position values 24 for the calibration mark 53 are captured, the method can be continued, by way of corresponding sub-steps, in any desired positions of the calibration object 52.

Figure 4B:
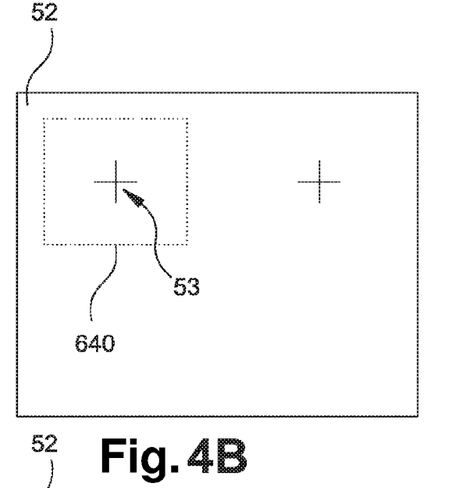
Figure 4C:
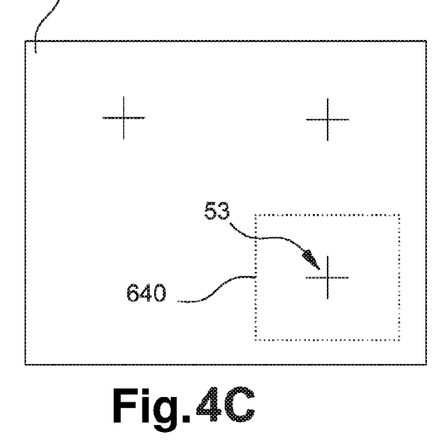
Figure 4D:
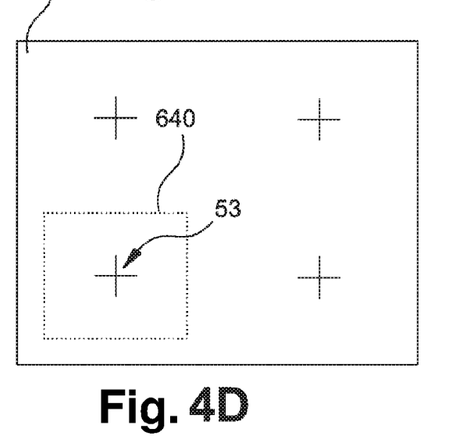

For example, in the sub-step shown in FIG. 4B, an additional calibration mark 53 is made in the left-hand upper region of the calibration object and (cf. the capturing region 640) is captured and evaluated. The same applies similarly to the sub-steps shown in FIGS. 4C and 4D which are carried out in a similar manner. Particularly reliable calibration values, which can be written into the calibration data store 20 shown in FIG. 2, for example, are obtained as a result of the fourfold calibration.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for calibrating a laser deflection device in a reflected light device of a microscope of a laser microdissection system including a digital image capturing unit comprising an image evaluation module, the method comprising:
   generating, by a laser unit of the laser microdissection system, a laser beam;
   guiding the laser beam through the reflected light device which includes the laser deflection device;
   guiding the laser beam through a microscope objective of the microscope after the laser beam passes through the reflected light device;
   directing the laser beam to a position in an object plane of the microscope objective by actuating the laser deflection device using first actuation signals which are calculated based on default position values and first calibration values for the laser deflection device;
   placing a calibration object in the object plane of the microscope objective;
   making at least one calibration mark on the calibration object using the laser beam;
   capturing an image of the calibration object by the digital image capturing unit;
   determining actual position values for the at least one calibration mark by the image evaluation module; and
   determining second calibration values for the laser deflection device based on a relationship between the default position values and the actual position values.

2. The method according to claim 1, wherein planar coordinates or polar coordinates are used for the default position values, the actual position values or the calibration values.

3. The method according to claim 1, wherein at least three calibration marks are made on the calibration object and actual position values are determined therefrom in each case.

4. The method according to claim 1, wherein the calibration object has a coating that can be processed by the laser beam and is applied to a microscope slide.

5. The method according to claim 1, wherein the at least one calibration mark on the calibration object is punctiform, circular, crosshair-shaped or cross-shaped.

6. The method according to claim 1, further comprising using the second calibration values to calculate second actuation signals, and directing the laser beam, in a post-calibration mode of the laser microdissection system, to a position in an object plane of the microscope objective by actuating the laser deflection device using the second actuation signals.

7. The method according to claim 1, wherein the image evaluation module uses at least one digital pattern recognition specification when determining the actual position values of the at least one calibration mark.

8. The method according to claim 1, the method further comprising adjusting at least one of an energy, a cutting speed or an aperture of the laser beam based on at least one feature of the at least one calibration mark.

9. A laser microdissection system, comprising:
a laser unit configured to generate a laser beam;
a microscope having a reflected light device configured to guide the laser beam through a microscope objective of the microscope, the reflected light device including a laser deflection device configured to deflect the laser beam to a position in an object plane of the microscope objective using first actuation signals;
a digital image capturing unit including an image evaluation module; and
a calibration arrangement configured to calibrate the laser deflection device by:
actuating the laser deflection device using the first actuation signals which are calculated based on default position values and first calibration values for the laser deflection device,
making at least one calibration mark on a calibration object, which is placed in the object plane of the microscope objective using the laser beam,
subsequently capturing an image of the at least one calibration mark using the digital image capturing unit,
determining actual position values for the at least one calibration mark using the image evaluation module, and
determining second calibration values for the laser deflection device based on a relationship between the default position values and the actual position values.

* * * * *